US00PP34747P2

(12) United States Plant Patent
Horvath

(10) Patent No.: US PP34,747 P2
(45) Date of Patent: Nov. 15, 2022

(54) ***SOLIDAGO* PLANT NAMED 'SUGAR KISSES'**

(50) Latin Name: ***Solidago* hybrid**
Varietal Denomination: Sugar Kisses

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 17/803,113

(22) Filed: Feb. 22, 2022

(51) Int. Cl.
*A01H 5/02* (2018.01)
*A01H 6/14* (2018.01)

(52) U.S. Cl.
USPC ..... Plt./483

(58) Field of Classification Search
USPC ..... Plt./483
CPC ..... A01H 5/02; A01H 5/00; A01H 6/14
See application file for complete search history.

(56) References Cited

PUBLICATIONS

Quality Cuttings Team 2021-22 Catalog, retrieved on Mar. 9, 2022, retrieved from the Internet at https://qualitycuttings.com/wp-content/uploads/2021/07/2021-22-QCT-Catalog.pdf, pp. 1-5, 76, 110. (Year: 2022).*

Wisconsin State Herbarium, Flora of Wisconsin, retrieved on Mar. 9, 2022, retrieved from the Internet at https://wisflora.herbarium.wisc.edu/taxa/index.php?taxon=5093, one page. (Year: 2022).*

* cited by examiner

*Primary Examiner* — June Hwu

(57) ABSTRACT

A new and distinct variety of *Solidago* plant named 'Sugar Kisses' as illustrated and described, characterized by the combination of larger foliage, taller height, white ray florets and yellow disc florets.

1 Drawing Sheet

Figure 1:
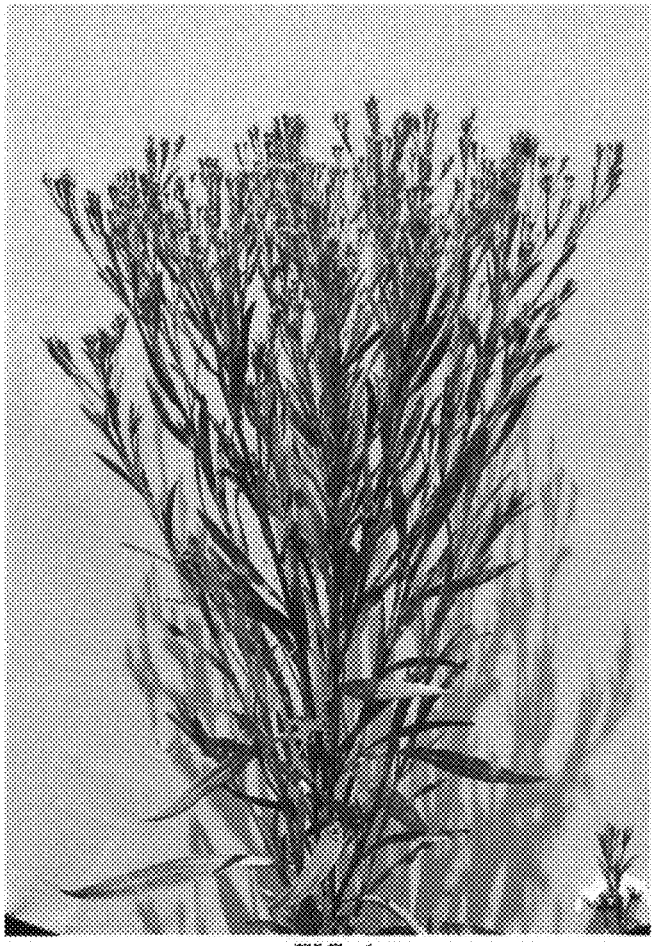

Latin name: *Solidago* hybrid.
Cultivar name: 'Sugar Kisses'.

BACKGROUND OF THE INVENTION

The present invention relates to a new and distinct hybrid of *Solidago* plant named 'Sugar Kisses' characterized by the combination of larger foliage, taller height, white ray florets and yellow disc florets compared to the seed parent. The new *Solidago* was raised as a seedling from open pollinated seed sown from the seed parent *Solidago ptarmicoides* plant, not patented, in Hebron, Ill. in 2019. The selection of the new plant was due to its' larger foliage, taller height, white ray florets and yellow disc florets compared to the seed parent. Initial asexual reproduction has taken place at a nursery in Hebron, Ill. since 2020 by means of division, and stem cuttings. The new *Solidago* has shown to be stable and identical in reproduction after rooting over 400 plants from 2020 to 2021. No plants of the new *Solidago* have been sold in this country, or anywhere in the world, prior to the tiling of this application, nor has any disclosure of the new plant been made prior to the filing of this application with the exception of that which was disclosed by the inventor and his company, Intrinsic Perennial Gardens, Inc and Quality Cuttings Team is a licensee of Intrinsic Perennial Gardens and who did obtain plants from the inventor within one year of filing of this application and was derived directly from the inventor.

SUMMARY OF THE INVENTION

The new *Solidago* plant named 'Sugar Kisses' characterized by the combination of larger foliage, taller height, white ray florets and yellow disc florets compared to the seed parent.

SUMMARY OF THE INVENTION

The new *Solidago* plant named 'Sugar Kisses' characterized by the combination larger foliage, taller height, and white and yellow bi-color flowers compared to the seed parent have been observed to be unique and stable.

Plants of the new *Solidago* can be compared to plants of *ptarmacoides* the seed parent, not patented.

1. The new *Solidago* plant has a mature size measuring 60 cm high and 45 cm wide while *Solidago ptarmicoides* measures 30 cm high and 30 cm wide.
2. The new *Solidago* plant has upright stems growing to 60 cm while ptarmicoides has a short mounding habit.
3. The new *Solidago* plant has larger foliage approximately 21 cm long and 17 mm wide while *Solidago ptarmicoides* has foliage that reaches approximately 15 cm long and 1 cm wide.

Plants of the new *Solidago* can also be compared to the *Solidago riddellii* not patented. The new plant has longer foliage, 21 cm in length with a glabrous texture while *Solidago riddellii* has foliage 5-10 cm in length and rough pubescent foliage. The new *Solidago* has white ray florets and yellow disc florets on 60 cm stems, while *Solidago riddellii* has golden yellow flowers on stems up to 85 cm in length.

Plants of the new *Solidago* can also be compared to the *Solidago ohioensis* not patented. The new plant has longer foliage, 21 cm in length while *Solidago ohioensis* has foliage 7-10 cm in length. The new *Solidago* has white ray florets and yellow disc florets on 60 cm stems, while *Solidago ohioensis* has golden yellow flowers on stems up to 120 cm in length.

DESCRIPTION OF PHOTOGRAPHS

Figure 2:
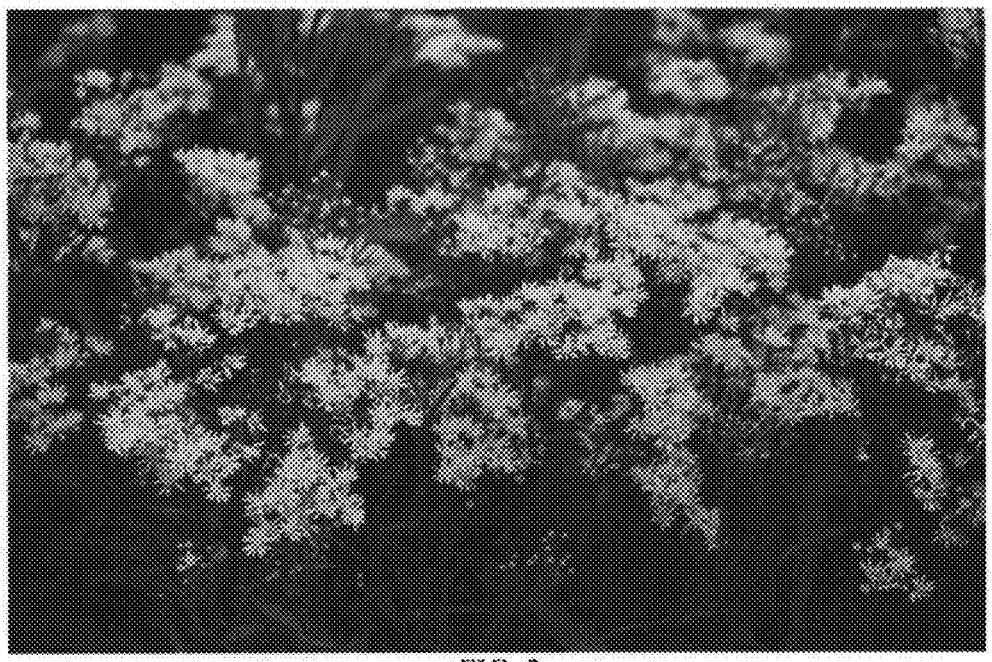

FIG. 1. A budded stem on a 2 year old plant in July.
FIG. 2. A flowering plant in August.

DETAILED BOTANICAL DESCRIPTION

In the following description, color references are made to The Royal Horticultural Society Colour Chart 2001 edition. Plants used for the description were grown for two seasons at a nursery in Hebron, Ill. Measurements and numerical values represent averages of typical plants.

Botanical classification: *Solidago* hybrid 'Sugar Kisses'.

Parentage: Male or pollen parent an unknown *Solidago*, female or seed parent, *Solidago ptarmicoides*.

Propagation: Vegetative division and stem cutting propagation.

Root description: Fibrous, thin thickness, white in color.

Root habit: Moderate branching, moderate density.

Plant description: Herbaceous perennial. Overall habit of the new *Solidago* is an upright clump, with branching stems topped by white ray florets and yellow disc florets starting in August.

- *Plant height.*—60 cm.
- *Plant width.*—48 cm.
- *Primary stem diameter.*—8 mm.
- *Primary and secondary stem description.*—Branching, with 20 or more leaves per secondary stem. Leaves get smaller as they go up the stem. Strength — strong.
- *Primary and lateral stem texture.*—Glabrous.
- *Secondary stem description.*—Average 10 lateral stems per primary stem.
- *Secondary stem length.*—25 cm.
- *Secondary stem diameter.*—2 mm.
- *Secondary stem internodes.*—1-4 cm.
- *Stem color.*—146 A maturing to close to N200 A.

Foliage:

- *Type.*—Herbaceous.
- *Leaf arrangement.*—Alternate, simple, sessile.
- *Length.*—21 cm.
- *Width.*—17 mm.
- *Shape.*—Lanceolate.
- *Apex.*—Acute.
- *Base.*—Accuminate.
- *Margin.*—Dentate.
- *Texture.*—Glabrous.
- *Venation.*—Pinnate. Venation Color — 146 D.
- *Adaxial leaf description.*—Color is 146 A including developing, fully expanded.
- *Abaxial leaf description.*—Color is 146 A including developing, fully expanded.

Bud:

- *Bud shape.*—Ligulate.
- *Bud length.*—5-6 mm.
- *Bud diameter.*—3-4 mm.
- *Bud color.*—146 D.

Inflorescence:

- *Inflorescence type.*—Compound corymb.
- *Position.*—Borne on both terminal and axillary peduncles above the foliage.
- *Number of flowers per inflorescences.*—Approximately 2200.
- *Arrangement.*—Disc and ray florets.
- *Mature center disc.*—5 mm wide and 5 mm height.
- *Number of disc florets.*—20, number of ray florets 10.
- *Immature disc floret color.*—2 B.
- *Mature disc floret color.*—Brown 200 A.
- *Disc floret diameter.*—1 mm or less at apex, less than 1 mm at base.
- *Disc floret shape.*—Rotate.
- *Disc floret length.*—7 mm.
- *Disc floret width.*—1 mm.
- *Disc floret apex.*—Acute.
- *Disc floret margin.*—Entire.
- *Disc floret count.*—20.
- *Ray floret size.*—5 mm length and 2 mm width.
- *Ray floret color upon opening.*—Light yellow Adaxial and Abaxial 2 D and in full bloom — Adaxial 155 D and Abaxial 155 D.
- *Ray floret aspect.*—Upright, then perpendicular to the peduncle.
- *Ray floret shape.*—Linear.
- *Ray floret apex.*—Truncate.
- *Ray floret base.*—Accuminate.
- *Ray floret margin.*—Entire.
- *Ray floret count.*—Approximately 10 per inflorescence.
- *Ray floret texture.*—Both the upper and lower surfaces are smooth, glabrous.
- *Overall inflorescence size.*—16 cm or more across in diameter with ray florets, 26 cm in height.
- *Bloom period and duration.*—August into September. 4-6 weeks on the plant.
- *Blooming habit.*—Upright on 45-60 cm terminal flowering stems.

Phyllaries:

- *Number of phyllaries per inflorescence.*—10 average.
- *Length.*—5 mm.
- *Width.*—1 mm.
- *Shape.*—Lanceolate.
- *Apex.*—Mucronate.
- *Base.*—Fused.
- *Margin.*—Entire.
- *Texture.*—Both upper and lower surface glabrous.
- *Color.*—Adaxial 146 D and Abaxial 146 D.

Peduncles:

- *Length of both terminal and axillary peduncles.*—15 cm.
- *Diameter.*—6 mm.
- *Angle.*—Erect to about 15 degrees from vertical.
- *Strength.*—Strong, Texture — glabrous, Color — 146 A.

Reproductive organs:

- *Androecium.*—Quantity per disc floret, 5.
- *Filament length.*—6 mm.
- *Filament color.*—155 B.
- *Anther shape.*—Oblong.
- *Anther length.*—Less than 1 mm.
- *Anther color.*—8 A.
- *Pollen amount.*—Moderate.
- *Gynoecium.*—Present on ray and disc florets.
- *Pistils.*—One, length 7 mm, width less than 1 mm.
- *Stigma shape.*—Two parted, Stigma color — 8 A.
- *Style length.*—4 mm, Style color — 155 D.
- *Scent.*—No scent noticed.

Seed and fruit: None observed

Disease resistance: Resistance to diseases common to *Solidago* has not been observed on plants grown under nursery conditions.

Hardiness: Plants of the new *Solidago* have been observed to be hardy to USDA Zone 5.

I claim:

1. A new and distinct variety of *Solidago* plant named 'Sugar Kisses', substantially as illustrated and described, herein.

* * * * *